United States Patent [19]

Quarroz

[11] Patent Number: 4,609,734

[45] Date of Patent: Sep. 2, 1986

[54] PROCESS FOR THE PRODUCTION OF 2-HYDROXYPYRIDINES FROM 2-PYRIDINE CARBOXYLIC ACID-N-OXIDES

[75] Inventor: Daniel Quarroz, Visp, Switzerland

[73] Assignee: Lonza Ltd., Gampel, Switzerland

[21] Appl. No.: 549,784

[22] Filed: Nov. 8, 1983

[51] Int. Cl.$^4$ .................. C07D 213/30; C07D 213/55
[52] U.S. Cl. ................................ 546/290; 546/298; 546/299; 546/326
[58] Field of Search ............... 546/290, 326, 299, 298

[56] References Cited

U.S. PATENT DOCUMENTS 3,153,044 10/1964 Zaslowsky .................. 546/345
3,862,159 1/1975 Umezawa et al. ............ 546/321
3,920,657 11/1975 Beschke et al. .............. 546/345

FOREIGN PATENT DOCUMENTS 48-05591 2/1973 Japan ..................... 546/326

OTHER PUBLICATIONS

Chemical Abstracts, 90: 174689(e), 1979, Yu et al.
Chemical Abstracts, 88: 14171704m, 1978, Yu et al.
J. Org. Chemistry, 26, (1961), 428.
Bull. Chem. Soc. Japan 42, 3350, (1969).

*Primary Examiner*—Alan L. Rotman
*Attorney, Agent, or Firm*—Fisher, Christen & Sabol

[57] ABSTRACT

Process for the production of 2-hydroxypyridines having the formula:

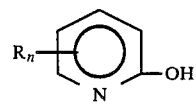

from 2-pyridine carboxylic acid-N-oxides having the formula:

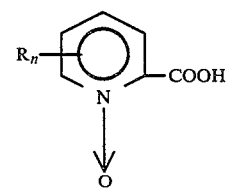

wherein R is H, a —COOH group, an alkyl group having 1 to 8 carbon atoms or an aryl group and n designates a number between 1 and 4. The N-oxide is converted using lower aliphatic carboxylic acid anhydrides in the presence of a tertiary amine. The conversion product is then hydrolyzed.

13 Claims, No Drawings

PROCESS FOR THE PRODUCTION OF 2-HYDROXYPYRIDINES FROM 2-PYRIDINE CARBOXYLIC ACID-N-OXIDES

BACKGROUND OF THE INVENTION

1. Field of the Invention

The invention relates to a process for the production of 2-hydroxypyridines, especially 2-hydroxypyridine carboxylic acid and 2-hydroxyalkyl pyridine.

2. Prior Art 2-hydroxypyridines can be obtained by diazotization of the corresponding amine pyridines and subsequent treatment with alkali lye. 2-hydroxypyridines can also be obtained from pyridine sulfonic acids or halogen pyridines by exchange with alkali, possibly by means of metal catalysts, such as, copper. The literature describes converting pyridine-N-oxide with acetic acid anhydride to 2-acetoxypyridine, which can be converted by hydrolysis into 2-hydroxypyridine or 2-pyridone. On the other hand, the reaction of picolinic acid-N-oxide with acetic acid anhydride only produces 2-hydroxypyridine in small quantities. Pyridine-N-oxide develops as the main product. [See J. Org. Chemistry, 26, (1961), 428.] Whenever the same reaction is carried out with isocinchomeronic acid-N-oxide, in an analogous manner only traces of 6-hydroxynicotinic acid are obtained and nicotinic acid-N-oxide is the main product. The reaction of 6-methylpicolinic acid-N-oxide, with acetic acid anhydride is an exception, which produces 2-hydroxy-6-methyl pyridine in a good yield. [See Bull. Chem. Soc. Japan 42, 3350, (1969).]

BROAD DESCRIPTION OF THE INVENTION

An object of the invention is to produce 2-hydroxypyridine carboxylic acids and 2-hydroxyalkyl pyridines in high yields. Other objects and advantages of the invention are set out herein or are obvious herefrom to one ordinarily skilled in the art.

The objects and advantages of the invention are achieved by the process of the invention.

The invention involves a process for the production of a 2-hydroxypyridine having the formula:

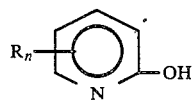

from a 2-pyridine carboxylic acid-N-oxide having the formula:

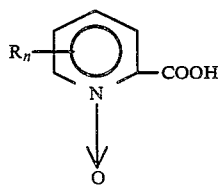

wherein R is H, —COOH, an alkyl group having one to eight carbon atoms or an aryl group and n is a number between 1 and 4. The 2-pyridine carboxylic acid-N-oxide is converted using a lower aliphatic carboxylic acid anhydride in the presence of a tertiary amine to a conversion product. The conversion product is hydrolyzed or saponified to produce the 2-hydroxypyridine.

Preferably the carboxylic acid anhydride is acetic anhydride. Also preferably the tertiary amine is triethyl amine. The ratio of tertiary amine to 2-pyridine carboxylic acid-N-oxide preferably lies between 1 to 1 and 20 to 1 and most preferably between 2 to 1 and 5 to 1. The reaction preferably is carried out at a temperature of 0° to 80° C. and most preferably between 20° and 60° C. Preferably the reaction is conducted in the presence of a solvent.

When 2-pyridine carboxylic acid-N-oxide is reacted with lower aliphatic carboxylic acid anhydrides in the presence of a tertiary amine, for example, triethyl amine, at a temperature of 20° to 60° C. and subsequently the intermediate is saponified, the 2-acetoxypyridine is formed.

The invention also involves a composition containing a 2-pyridine carboxylic acid-N-oxide having the formula:

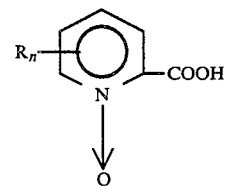

wherein R is H, —COOH, an alkyl group having 1 to 8 carbon atoms or an aryl group, a lower aliphatic carboxylic acid anhydride and a tertiary amine. A solvent can also be present in the composition.

The invention involves a process for the prodiction of a 2-hydroxypyridine having the formula:

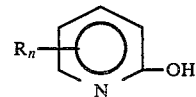

from a 2-pyridine carbosylic acid-N-oxide having the formula:

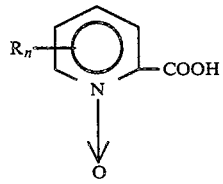

wherein (i) R is H or an alkyl selected from the group consisting of methyl, ethyl, octyl, butyl, propyl, isopropyl, isobutyl, 3-methyl-1-butyl, 2-butyl, 2-pentyl, heptyl, 2-methyl-2-butyl, hexyl, 2-ethyl-1-butyl, 2-methyl-1-butyl, 3-methyl-1-pentyl, 1-pentyl, isohexyl, 2-hexyl and 3-methyl-2-pentyl, and n is 1 to 4, (ii) R is —COOH, R is located in the 3-, 4-, 5-, or 6-postion, and n is 1, (iii) n is 2, R is —COOH, and the two Rs are in the 3- and 4-positions, the 4- and 5-positions and the 4- and 6-positions, (iv) R is phenyl, and n is 1, (v) R is naphthyl, and n is 1, or (vi) R is benzyl, and n is 1, comprising (a) converting the 2-pyridine carboxylic acid-N-oxide using a lower aliphatic carboxylic acid anhydride in the presence of a tertiary amine to a conversion product and (b) saponifying the conversion product to produce the 2-hydroxypyridine. The carboxylic acid anhydride can be acetic anhydride. The tertiary amine can be triethylamine. The molar ratio of the tertiary amine to the 2-pyridine carboxylic acid-N-oxide can be between 1 to 1 and 20 to 1. The conversion can be carried out in the presence of a solvent. The tertiary amine can be triethylamine. The molar ratio of the tertiary amine to the 2-pyridine carboxylic acid-N-oxide can be between 1 to 1 and 20 to 1. The molar ratio of the tertiary amine to the 2-pyridine carboxylic acid-N-oxide can be from 2 to 1 to 5 to 1. The conversion can be carried out at a temperature of 0° to 80° C. The conversion can be carried out at a temperature of 20° to 60° C. The conversion can be carried out in the presence of a solvent. The saponification can be conducted using KOH or NaOH. The invention involves a composition comprised of (i) a 2-pyridine carboxylic acid-N-oxide having the formula:

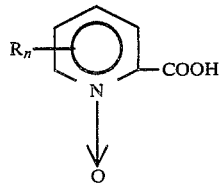

wherein (a) R is H or an alkyl selected from the group consisting of methyl, ethyl, octyl, butyl, propyl, isopropyl, isobutyl, 3-methyl-1-butyl, 2-butyl, 2-pentyl, heptyl, 2-methyl-2-butyl, hexyl, 2-ethyl-1-butyl, 2-methyl-1-butyl, 3-methyl-1-pentyl, 1-pentyl, isohexyl, 2-hexyl and 3-methyl-2-pentyl, and n is 1 to 4, (b) R is —COOH, R is located in the 3-, 4-, 5- or 6-position, and n is 1, (c) n is 2, R is —COOH, and the two Rs are in the 3- and 4-positions, the 4- and 5-positions and the 4- and 6-positions, (d) R is phenyl, and n is 1, (d) R is phenyl, and n is 1, (e) R is naphthyl, and n is 1, or (f) R is benzyl, and n is 1, (ii) a lower aliphatic carboxylic acid anhydride and (iii) a tertiary amine. A solvent can be also present. The molar ratio of the tertiary amine to the 2-pyridine carboxylic acid-N-oxide can be between 1 to 1 and 20 to 1. The molar ratio of the tertiary amine to the 2-pyridine carboxylic acid-N-oxide can be from 2 to 1 to 5 to 1. The lower aliphatic carboxylic acid anhydride can be propionic acid anhydride, n-butyric acid anhydride, valeric acid anhydride, caproic acid anhydride, oenanthic acid anhydride, caprylic acid anhydride, isobutyric acid anhyride, trimethylacetic acid anhydride, isocaproic acid anhydride, diethyl acetic acid anhydride, dimethylethylacetic acid anhydride, n-nonanoic acid anhydride, 2-ethlhexanoic acid anhydride or lauric acid anhydride. The tertiary amine can be triethylamine, tri-n-butylamine, trimethylamine, tributylamine, diethylmethyl amine, benzylethylphenylamine, benzylmethylphenylamine, dibenzylphenylamine, tributylamine, tripropylamine or diphenylmethylamine.

DETAILED DESCRIPTION OF THE INVENTION

The lower aliphatic anhydrides usually have 2 to 8 carbon atoms. The preferred low aliphatic anhydride is acetic acid anhydride. Examples of useful lower aliphatic anhydrides are propionic acid anhydride, n-butyric acid anhydride, valeric acid anhydride, caproic acid anhydride, oenanthic acid anhydride, caprylic acid anhydride, isobutyric acid anhydride, trimethylacetic acid anhydride, isocaproic acid anhydride, diethyl acetic acid anhydride, dimethylethylacetic acid anhydride, n-nonanoic acid anhydride, 2-ethylhexanoic acid anhydride and lauric acid anhydride. The carboxylic acid anhydride, in relation to the pyridine carboxylic acid-N-oxide, is used in 1 to 10 times molar excess and can also serve as the solvent.

According to the invention process 2-hydroxypyridine carboxylic acids are surprisingly obtained at high yields, with the reaction occurring at an extremely fast speed at relatively low temperatures.

The process of the invention can also be carried out in the presence of organic or inorganic solvents, such as toluene, petroleum ether, CCl₄, acetic acid ethyl ester, acetonitrile, n-hexane, cyclohexane, xylene, n-heptane, ethyl benzene, isopropylbenzene, n-octane, nitromethane, nitroethane, methyl cellosolve acetate, cellosolve acetate, methylene chloride, chlorobenzene, chlorotoluene, trichloroethane, methyl acetate, methyl formate, ethyl formate, n-propyl acetate, isopropyl acetate, n-butyl acetate, isobutyl acetate and nitrobenzene. The useful solvents include hydrocarbon solvents, halogenated solvents, ester solvents, ether solvents, nitrohydrocarbon solvents and the like, provided they are liquid in at least part of the temperature range used in the invention process.

Beside triethylamine, other aliphatic or aliphatic-/aromatic tertiary amines, pyridine or DMF can be used as a catalyst in the process. Examples of other useful tertiary amines are tri-n-butylamine, trimethylamine, tributylamine, diethylmethyl amine, benzylethylphenylamine, benzylmethylphenylamine, dibenzylphenylamine, tributylamine, tripropylamine and diphenylmethylamine. Trialkylamines are particularly useful catalysts. Preferably triethylamine is used and is applied in a molar ratio of tertiary amine to pyridine carboxylic acid-N-oxide of between 1 to 1 and 10 to 1, and preferably of between 2 to 1 and 5 to 1.

Beside 2-pyridine monocarboxylic acid-N-oxide, the corresponding pyridine dicarboxylic acid-N-oxides, such as, pyridine carboxylic acid-(2,3)-N-oxide(quinolinic acid), pyridine carboxylic acid-(2,4)-N-oxide(lutidinic acid), pyridine dicarboxylic acid-(2,5)-N-oxide(isocinchomeronic acid) and pyridine dicarboxylic acid-(2,6)-N-oxide(dipicolinic acid), and the corresponding pyridine dicarboxylic-N-oxides, such as, pyridine tricarboxylic acid-(2,3,4)-N-oxide (α-carbocinchomeronic acid), pyridine tricarboxylic acid-(2,4,5)-N-oxide(berberonic acid), pyridine tricarboxylic acid-(2,4,6)-N-oxide(trimesitic acid) and pyridine pentacarboxylic acid-N-oxide, can be used.

The pyridine carboxylic acid-N-oxides can be coresubstituted 1 to 4 times with an alkyl group having 1 to 8 carbon atoms or an aryl group. Examples of useful alkyl groups are methyl, ethyl, octyl, butyl, propyl, isopropyl, isobutyl, 3-methyl-1-butyl, 2-butyl, 2-pentyl, heptyl, 2-methyl-2-butyl, hexyl, 2-ethyl-1-butyl, 2-methyl-1-butyl, 3-methyl-1-pentyl, 1-pentyl, isohexyl, 2-hexyl and 3-methyl-2-pentyl. Examples of useful aryl groups are phenyl and naphthyl. An example of a useful alkaryl groups is benzyl.

The conversion reaction is carried out at a temperature of 0° to 80° C., preferably at 20° to 60° C.

By way of summary, 2-hydroxypyridines are produced from 2-pyridine carboxylic acid-N-oxides by reaction with acetic acid anhydride and tertiary amine.

EXAMPLE 1

Production of 6-hydroxynicotinic acid (6-OHNS) from isocinchomeronic acid-N-oxide (ICSO).

200 g of acetic acid anhydride (1.96 mole) and 50 g of triethylamine (0.5 mole) were put up, and 36 g of ICSO (0.197 mole) was dosed in by portions at ambient temperature in such a way that the reaction temperature did not exceed 30° C. After completion of the addition, the mixture was allowed to react again for about 1 hour at 30° C. until $CO_2$ no longer escaped. The resultant brownish-black solution was concentrated on a rotavapor (30 torr, 60° C.), and the viscous residue was saponified by the addition of 20 percent KOH (end pH≅12) at 80° C. for ¼ hour. To remove the triethyl amine, the liquid reaction mixture was extracted with $CH_2Cl_2$ and subsequently acidified with concentrated HCl (pH 1). The precipitate obtained hereby was sucked off, washed with $H_2O$ and dried at 45° C. and 20 torr. The yield of 23 g (titrimerically determined content 96.5 percent) corresponded to 81 percent of theoretical.

EXAMPLE 2

Production of 2-hydroxynicotinic acid (2-OHNS) from quinolinic acid-N-oxide (CSO).

100 g of acetic acid anhydride (0.98 mole) and 25 g of triethylamine (0.25 mole) were put up and heated to 40° C. in order to ensure a lively development of gas during the addition by portions of 18 g of CSO (0.098 mole). The reprocessing of the reaction mixture took place analogously to Example 1. The yield was 5.6 g of pure 2-OHNS according to NMR (about 41 percent of theoretical).

EXAMPLE 3

Production of 2-hydroxypyridine from 2-pyridine carboxylic acid-N-oxide(picolinic acid-N-oxide; PSO).

200 g of acetic acid anhydride (1.96 mole) and 40 g of triethylamine (0.4 mole) were put up in a flask and 36 g of PSO (0.26 mole) was added in doses. The reaction temperature during the addition of the PSO was kept between 20° and 30° C. After completion of the reaction, the fluid was evaporated on a rotavapor and the residue was absorbed with water. To this aqueous solution, 30 percent NaOH was added slowly until no further precipitate developed. The Na salt of the 2-hydroxy pyridine thus obtained was sucked off, was washed with 30 percent NaOH, was recrystallized from 95 percent alcohol and was dried at 45° C. and 20 torr. The yield was 30.5 g of pure hydroxypyridine-Na-salt according to H-NMR. Since the 2-hydroxypyridine-Na-salt still contained about 3 percent $H_2O$, this resulted in about 95 percent of theoretical.

EXAMPLE 4

Production of 6-hydroxynicotinic acid.

20.4 g of acetic acid anhydride (0.2 mole), 20.2 g of $Et_3N$ (0.2 mole) and 50 ml of $CCl_4$ were put up in a flask. 18.3 g of isocinchomeronic acid-N-oxide (0.1 mole) was added by portions to this solution. The temperature rose to 50° C. After completion of the reaction the solvents were distilled off. About 100 ml of 20 percent KOH was added drop by drop to the viscous residue and the acetate was saponified over a 15 minute period at 80° C. After removal of the $Et_3N$ by extraction, the aqueous solution was acidified with concentrated HCl. The precipitate was sucked off, washed with water and dried under a vacuum. 11.0 g of 6-hydroxy nicotinic acid was obtained, which was pure according to NMR. The crude yield was about 79 percent.

EXAMPLE 5

Production of 6-hydroxynicotinic acid.

Example 1 was repeated, except that propionic acid anhydride was used instead of acetic acid anhydride. The yield of 6-hydroxynicotinic acid was 78 percent.

EXAMPLE 6

Production of 6-hydroxynicotinic acid.

Example 1 was repeated, except that tributylamine was used instead of $Et_3N$. The yield of 6-hydroxynicotinic acid was 75 percent.

EXAMPLE 7

Production of 6-hydroxynicotinic acid.

Example 4 was repeated, except that petrolether was used instead of $CCl_4$. The yield of 6-hydroxynicotinic acid was 67 percent.

EXAMPLE 8

Production of 6-hydroxy picolinic acid.

Acetic acid anhydride (0.5 mole) and $Et_3N$ (0.15 mole) were put up in a flask. Dipicolinic acid-N-oxide (0.05 mole) was put into this solution by portions; the temperature amounted to 35° C. After completion of the addition, the solution was concentrated by evaporation on a rotavapor. 80 ml of 20 percent KOH was added to the residue and was kept for 15 minutes at 80° C. After extraction of the $Et_3N$ with $CH_2Cl_2$, the aqueous phase was acidified with HCl concentrated to pH 2. The crystals were sucked off, washed with water and dried. 4.2 g of 6-hydroxypicolinic acid was obtained and was pure according to NMR. The crude yield was about 60 percent.

EXAMPLE 9

Production of 6-methylpyridone-2.

Acetic acid anhydride (0.5 mole) and $Et_3N$ (0.15 mole) were put up in a flask. To this was added by portions 9.1 g (0.59 mole) of 6-methylpicolinic acid-N-oxide. During the addition the temperature rose up to 45° C. After completion of the $CO_2$-development, the black solution was evaporated on a rotavapor. The residue was carefully hydrolyzed with concentrated HCl (115 ml) and the acetate was saponified for 5 hours at 90° C. After distilling off the aqueous solution, the residue was adjusted basically (pH 7-8) with KOH and the 6-methylpyridone-2 was extracted with $CH_2Cl_2$. 3.7 g of this product were isolated and was pure according to NMR. The yield was about 57 percent.

What is claimed is:

1. Process for the production of 2-hydroxypyridine having the formula:

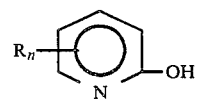

from a 2-pyridine carboxylic acid-N-oxide having the formula:

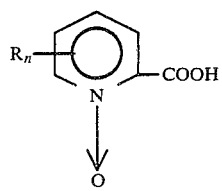

wherein (i) R is H or an alkyl selected from the group consisting of methyl, ethyl, octyl, butyl, propyl, isopropyl, isobutyl, 3-methyl-1-butyl, 2-butyl, 2-butyl, 2-pentyl, heptyl, 2-methyl-2-butyl, hexyl, 2-ethyl-1-butyl, 2-methyl-1-butyl, 3-methyl-1-pentyl, 1-pentyl, isohexyl, 2-hexyl and 3-methyl-2-pentyl, and n is 1 to 4, (ii) R is —COOH, R is located in the 3-, 4-, 5- or 6-position, and n is 1, (iii) n is 2, R is —COOH, and the two Rs are in the 3- and 4-positions, the 4- and 5-positions and the 4- and 6-positions, (iv) R is phenyl, and n is 1, (v) R is napthyl, and n is 1, or (vi) R is benzyl, and n is 1, comprisng (a) converting the 2-pyridine carboxylic acid-N-oxide using a lower aliphatic carboxylic acid anhydride in the presence of a tertiary amine to a conversion product and (b) saponifying the conversion product to produce the 2-hydroxypyridine.

2. Process as claimed claim 1 wherein the carboxylic acid anhydride is acetic anhydride.

3. Process as claimed in claim 2 wherein the tertiary amine is triethylamine.

4. Process as claimed in claim 3 wherein the molar ratio of the tertiary amine to the 2-pyridine carboxylic acid-N-oxide is between 1 to 1 and 20 to 1.

5. Process as claimed in claim 4 wherein the conversion is carried out at a temperature of 0° to 80° C.

6. Process as claimed in claim 5 wherein the conversion is carried out in the presence of a solvent.

7. Process as claimed in claim 4 wherein the tertiary amine is triethylamine.

8. Process as claimed in claim 4 wherein the molar ratio of the tertiary amine to the 2-pyridine carboxylic acid-N-oxide is between 1 to 1 and 20 to 1.

9. Process as claimed in claim 4 wherein the molar ratio of the tertiary amine to the 2-pyridine carboxylic acid-N-oxide is from 2 to 1 to 5 to 1.

10. Process as claimed in claim 4 wherein the conversion is carried out at a temperature of 0° to 80° C.

11. Process as claimed in claim 1 wherein the conversion is acrried out at a temperature of 20° to 60° C.

12. Process as claimed in claim 1 wherein the conversion is carried out in teh presence of a solvent.

13. Process as claimed in claim 1 wherein the saponification is conducted using KOH or NaOH.

* * * * *